(12) United States Patent
Campisi et al.

(10) Patent No.: US 9,731,019 B2
(45) Date of Patent: Aug. 15, 2017

(54) RELEASE SYSTEM OF HYDROPHOBIC PROTEINS

(71) Applicant: FIDIA FARMACEUTICI S.P.A., Abano Terme (IT)

(72) Inventors: Monica Campisi, Abano Terme (IT); Cristian Guarise, Abano Terme (IT); Davide Renier, Abano Terme (IT)

(73) Assignee: FIDIA FARMACEUTICI S.P.A., Abano Terme (PD) (IT)

( * ) Notice: Subject to any disclaimer, the term of this patent is extended or adjusted under 35 U.S.C. 154(b) by 0 days.

(21) Appl. No.: 14/404,138

(22) PCT Filed: May 30, 2013

(86) PCT No.: PCT/IB2013/054477
§ 371 (c)(1),
(2) Date: Nov. 26, 2014

(87) PCT Pub. No.: WO2013/179258
PCT Pub. Date: Dec. 5, 2013

(65) Prior Publication Data
US 2015/0290326 A1    Oct. 15, 2015

(30) Foreign Application Priority Data

May 31, 2012   (IT) .............................. PD2012A0173

(51) Int. Cl.

| | |
|---|---|
| *A61K 47/36* | (2006.01) |
| *A61K 38/22* | (2006.01) |
| *A61K 9/00* | (2006.01) |
| *A61K 38/57* | (2006.01) |
| *A61K 38/38* | (2006.01) |
| *A61K 38/27* | (2006.01) |
| *A61K 38/20* | (2006.01) |
| *A61K 38/18* | (2006.01) |
| *A61K 38/23* | (2006.01) |
| *A61K 38/19* | (2006.01) |
| *A61K 9/06* | (2006.01) |
| *C08B 37/08* | (2006.01) |
| *C08L 89/00* | (2006.01) |
| *C08L 5/08* | (2006.01) |
| *A61K 38/28* | (2006.01) |
| *A61K 38/46* | (2006.01) |

(52) U.S. Cl.
CPC ............ *A61K 47/36* (2013.01); *A61K 9/0019* (2013.01); *A61K 9/06* (2013.01); *A61K 38/2006* (2013.01); *A61K 38/2235* (2013.01); *A61K 38/27* (2013.01); *A61K 38/28* (2013.01); *A61K 38/465* (2013.01); *C08B 37/0072* (2013.01); *C08L 5/08* (2013.01); *C08L 89/00* (2013.01)

(58) Field of Classification Search
None
See application file for complete search history.

(56) References Cited

U.S. PATENT DOCUMENTS 7,863,256 B2 *  1/2011  Schiavinato ......... A61K 31/728
                                                        424/488
2010/0158796 A1  6/2010  Bellini et al.

FOREIGN PATENT DOCUMENTS

EP         1 095 064 A1   5/2001
WO    WO 2006/092233 A1   9/2006

OTHER PUBLICATIONS

Kim et al. Development of a novel sustained release formulation of recombinant human growth hormone using sodium hyaluronate microparticles. J Control Release. May 18, 2005;104(2):323-35. Epub Apr. 7, 2005.*

Kim et al. Additive effects of intra-articular injection of growth hormone and hyaluronic acid in rabbit model of collagenase-induced osteoarthritis. J Korean Med Sci. May 2010;25(5):776-80. Epub Apr. 16, 2010.*

Borzacchiello et al., "Effect of hyaluronic acid amide derivative on equine synovial fluid viscoelasticity", Journal of Biomedical Materials Research Part A, XP-002619476, vol. 92A, No. 3, Mar. 1, 2010, pp. 1162-1170.

* cited by examiner

*Primary Examiner* — David Romeo
(74) *Attorney, Agent, or Firm* — Birch, Stewart, Kolasch & Birch, LLP

(57) ABSTRACT

The object of the present invention is novel release systems comprising specific hyaluronic acid amides combined with therapeutically and/or biologically active proteins with a mainly hydrophobic nature, for sustained, slow release over time which increases the efficacy of the medicament and the patient's compliance.

16 Claims, 11 Drawing Sheets

Amino acid scale hydropathicity values:

Ile: 4.500

Val: 4.200

Leu: 3.800

Phe: 2.800

Cys: 2.500

Met: 1.900

Ala: 1.800

Gly: -0.400

Asn: -3.500

Thr: -0.700

Trp: -0.900

Ser: -0.800

Tyr: -1.300

Pro: -1.600

His: -3.200

Glu: -3.500

Asp: -3.500

Gln: -3.500

Lys: -3.900

Arg: -4.500

FIGURE 1

RELEASE SYSTEM OF HYDROPHOBIC PROTEINS

The present invention relates to pharmaceutical compositions comprising specific hyaluronic acid amides combined with proteins of a mainly hydrophobic nature, which are therapeutically and/or biologically active, for the preparation of sustained, slow protein release systems.

BACKGROUND TO THE INVENTION

The first medicament to be obtained by engineering a living (bacterial) system was insulin, approved by the Food and Drug Administration (FDA) in 1982. Human growth hormone, previously extracted from cadavers, was also rapidly engineered. In 1986 the FDA approved the first recombinant human vaccine, against hepatitis B. The industrial production of medicaments using living systems as bioreactors has become widespread since then, and is now the preferred synthesis method for numerous medicaments, especially due to the relatively low manufacturing cost.

Many human proteins designed for therapeutic (and non-therapeutic) use are produced by bioengineering technology, including erythropoietin (for the treatment of anaemia), interleukin 2 (for the treatment of renal carcinoma), IL-1Ra (IL-1 receptor antagonist), glucagon, interferon, human DNase enzyme, calcitonin and many others.

Said medicaments mainly have a protein or polypeptide nature, and are generally administered parenterally, because oral administration would cause rapid degradation of the active ingredient. However, parenteral administration can cause problems with patient compliance because of the repeated administrations required to ensure therapeutic efficacy. These proteins generally have a very short half-life; for example, the growth hormone hGH (genetically produced) requires daily injections. Consequently, to reduce the number of administrations and increase patient compliance, many experiments have been conducted to develop systems for the release of proteins/medicaments with an increased half-life.

Said release systems must guarantee that the activity of the medicament is maintained, and must therefore ensure that the three-dimensional structure of the protein/medicament remains intact; however, stress situations which can occur during their preparation, such as the presence of organic solvent and/or variations in temperature and pH, can cause deamidation or oxidation of the protein chain, leading to denaturing and loss of therapeutic activity.

For example, the use of PLGA (polylactic/glycolic acid) microspheres is known as a release system for small peptides, with excellent results (Hutchinson F. G., Biochem. Soc. Trans., 1985, 13:520-523); however, its use to formulate a depot in the release of hGH was impossible, because the denaturing of the protein created inflammatory problems.

The continual search for protein/medicament release systems devoid of toxicity but with unchanged efficacy of the active ingredient delivered has led to the use of natural polymers for formulations which (due to their combination with the active ingredient) can present a modification in the kinetics of the medicament with which they are combined.

Hyaluronic acid (HA) is a heteropolysaccharide composed of alternate residues of D-glucuronic acid and N-acetyl-D-glucosamine. It is a natural straight-chain polymer with a molecular weight ranging between 50,000 and $13 \times 10^6$ Da, depending on the source from which it is obtained and the preparation methods used.

It is present in nature in pericellular gels, in the ground substance of the connective tissue of vertebrates (of which it is one of the main components), and in the synovial fluid of the joints, the vitreous humour and the umbilical cord.

HA therefore plays an important biological part in living organisms by providing a mechanical support for the cells of many tissues, such as skin, tendons, muscles and cartilage.

Due to its properties, hyaluronic acid protects the tissues against free radicals, controls inflammatory processes and stimulates angiogenesis, and has proved particularly effective in modulating all the main stages of wound-healing (EP 1196179).

The use of said polysaccharide as a carrier of various kinds of medicaments is known, in simple combination or salified with hyaluronic acid, because its particular properties of biocompatibility, biodegradability, non-immunogenicity, viscosity and hydratability make it particularly suitable as a release system for medicaments and molecules at both topical and systemic level (EP 197718, EP 445255). Said polysaccharide has also been studied as a drug delivery for specific proteins, such as IL-1Ra (U.S. Pat. No. 6,096, 728), erythropoietin (Hahn S K. et al., Int J Pharm., 2006, 28, 322:44-51), insulin (Nomura M. et al., J Pharm Pharmacol, 1994, 46:768-770), growth hormone (Kim S J. et al., Journal of Controlled Release, 2005, 104:323-335), interferon and follicle-stimulating hormone (U.S. Pat. No. 8,025, 900).

In all these cases, the combination of the medicament with the polysaccharide has led to "slow" release of the protein carried, but not slow enough to reduce the number of administrations of the medicament.

HA is a completely natural polysaccharide which is rapidly degraded by the enzymes present in the body (hyaluronidase), releasing the medicament with which it is combined relatively rapidly. For these reasons, the carboxyl and hydroxyl groups of HA have been chemically modified to give rise to crosslinked derivatives (U.S. Pat. Nos. 4,582, 865; 4,713,448; 5,676,964; 4,957,74; 5,827,937) or derivatised with other natural or synthetic polymers, or with molecules of various sizes and physicochemical characteristics (U.S. Pat. No. 4,851,521); however, the preparation processes of said derivatives often prejudice the integrity of the pharmacological agent conveyed.

BRIEF DESCRIPTION OF THE DRAWINGS

FIG. 1: Scale of hydropathicity values for amino acids.

DESCRIPTION OF THE INVENTION

Figure 2:
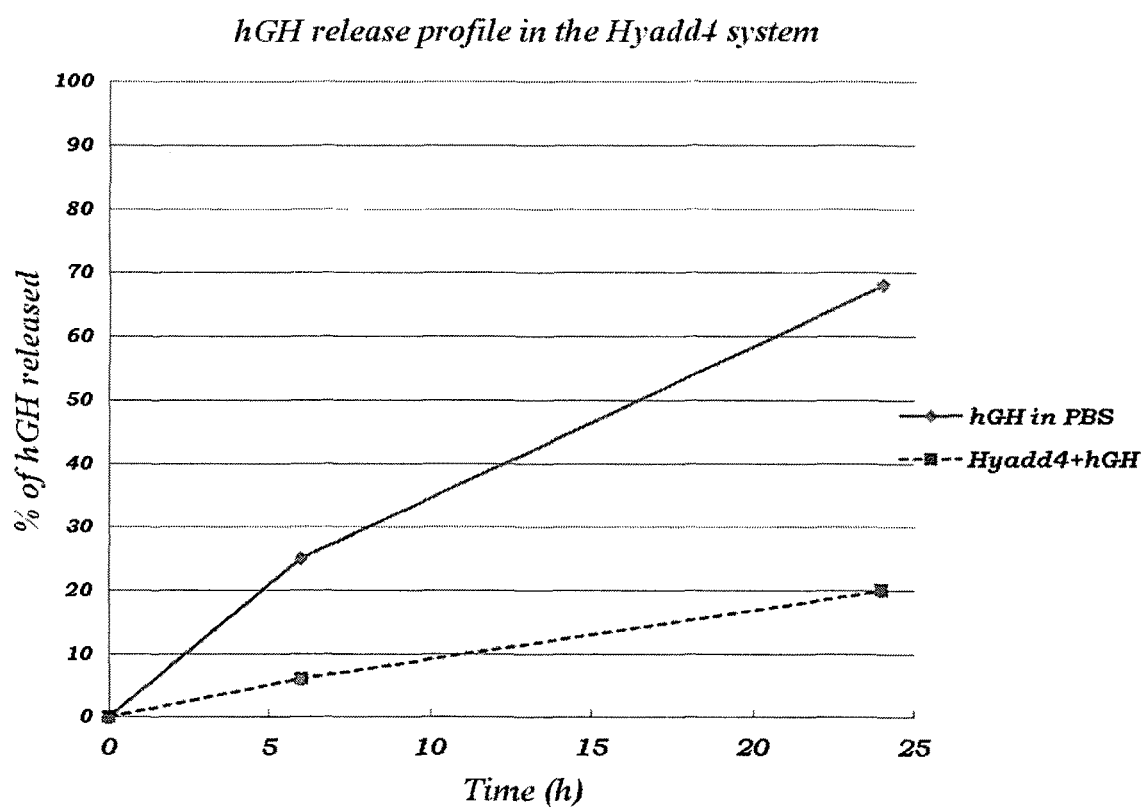
FIG. 2: Release profile of hGH determined by the system formed by Hyadd4 and hGH vs the control represented by the same protein prepared in PBS.

The object of the invention is novel release systems comprising specific hyaluronic acid amides in association with therapeutically and/or biologically active proteins with a mainly hydrophobic nature, for sustained, slow release over time which increases the efficacy of the medicament and the patient's compliance.

Some examples of therapeutically and/or biologically active proteins with a mainly hydrophobic nature, according to the invention, are listed below:

Insulin is a protein hormone with anabolic properties, produced by the beta cells of the islets of Langerhans in the pancreas; it consists of two chains joined by two sulphide bridges. Its best-known function is regulation of the blood glucose levels. This protein is therefore used to treat type 1 or type 2 diabetes with very little or no insulin production. The hormone is administered by subcutaneous injection (because if it is injected directly into the bloodstream, absorption of the medicament is too rapid, possibly leading to hypoglycaemia). The therapeutic approach is based on a variable daily number of blood glucose tests performed by the patient, with consequent administration of insulin at calibrated doses (3 or more).

Growth hormone (GH) is a peptide hormone of the anterior pituitary consisting of 191 amino acids and weighing 22,005 Da. Its main function is to stimulate the development of the human body (and those of many other vertebrates) by promoting the growth and mitotic division of the cells of nearly all the body tissues (in particular it promotes the growth of bone, cartilage and connective tissue).

During infancy, hyposecretion of GH causes pituitary dwarfism, while hypersecretion causes pituitary gigantism. If the hypersecretion begins after growth has ended, generally due to a tumour, acromegaly develops, wherein the bones of the face, hands and feet are considerably enlarged.

It is therefore used for patients still at the growth stage and adults suffering from pituitary tumours.

GH is also used to treat disorders not caused by a deficit of GH, such as Turner syndrome, chronic kidney disease, ISS (idiopathic short stature) and multiple sclerosis, and to increase weight loss in obese patients, in fibromyalgia, in Crohn's disease and ulcerative colitis.

Intra-articular administration of hGH was recently tested with excellent results in the treatment of osteoarthritis (OA), also demonstrating the efficacy of said hormone in repairing cartilage damage caused by OA (EP1153607; Kim S B et al., J Korean Med Sci., 2010, 25:776-80).

Calcitonin (CT) is a hormone consisting of a 32-amino-acid polypeptide produced, in humans, by the parafollicular cells (also known as C cells) of the thyroid. The main function of calcitonin is to lower the calcium concentration in the blood by counteracting the effects of parathyroid hormone parathormone. This calcium regulation mechanism has been found in fish, reptiles, birds and mammals. The hormone calcitonin also acts at renal level, stimulating the tubular elimination of calcium. sCT (salmon CT) is generally used to treat osteoporosis, hypercalcaemia, bone metastases and Paget's disease.

Once again, recent experimental data have demonstrated the effectiveness of calcitonin in the treatment of osteoarthritis: its administration has proved to protect the joint surfaces against erosion caused by OA (Manicourt D H et al., J Musculoskelet Neuronal Interact, 2005, 5(3):285-293).

IL1-Ra is the receptor antagonist of cytokine IL-1, a potent inducer of local and systemic inflammatory processes. IL-1 is mainly produced by the B and T lymphocytes and macrophages after bacterial stimulus or stimulation by other cytokines; it is also secreted by the alveolar macrophages, endothelial, epithelial and smooth muscle cells, fibroblasts, osteoclasts, synoviocytes and many other cell types. IL-1 is involved in particularly serious disorders like psoriasis and septic shock, and in the pathogenesis of some types of tumour. In combination with other cytokines, IL-1 represents one of the major mediators of the inflammatory processes, and is thus involved in many disorders like osteoporosis, rheumatoid arthritis (RA), psoriatic arthritis and osteoarthritis (OA): in fact, large amounts of IL-1 have been found in the synovial fluid of patients suffering from rheumatoid arthritis and/or osteoarthritis.

The expression of IL-1 is crucial to the pathogenesis of OA, as. IL-1 promotes the synthesis, secretion and activation of the metalloproteases (MMP), protease enzymes produced by the chondrocytes, which are responsible for the degradation of cartilage matrix.

All the experimental data relating to the OA process strongly support the concept that IL-1 and TNFα represent the main catabolic system involved in the destruction of the joint tissues; in fact, it has been demonstrated that by blocking the production and/or activation of IL-1, the destruction of joint matrix is prevented and/or reduced (Caron J. P. et al., Arthritis Rheum, 1996, 39:1535-1544).

New medicaments containing the receptor antagonist IL-1Ra are currently used to counteract the effects of this cytokine, because blocking the receptor has proved to be an effective way of treating disorders wherein IL-1 is implicated (Burger D. et al., *Cytokine Reference*, Oppenheim J and Feldmann M, Eds. New York, London, Academic Press, 2000, p. 31-336; Jiang Y. et al., Arthritis Rheum, 2000, 43(5):1001-9).

IL-1Ra is a protein that acts as an inhibitor of said interleukin; however, medicaments containing IL-1Ra (such as Kineret® based on anakinra, the recombinant non-glycosylated form of the human protein IL-1Ra), have a very short half-life, which often prejudices the clinical result. It is therefore important to formulate a novel pharmaceutical composition containing IL-1Ra in order to deliver the medicament in a sustained, slow way, guaranteeing a longer half-life to ensure consolidated clinical results.

Granulocyte-colony stimulating factor (G-CSF) is a 174-180 amino-acid glycoprotein that stimulates bone marrow to produce granulocytes and stem cells which are subsequently released into the bloodstream. This growth factor has proved active as neurotrophin, and is therefore currently being studied for the treatment of cerebral ischaemia and amyotrophic lateral sclerosis. It is normally used for oncological patients, to counteract the neutropenia associated with chemotherapy; finally, recent experimental studies have demonstrated that intravenous treatment with G-CSF promotes the regeneration of damaged cardiac cells.

Platelet-derived growth factor (PDGF) is a biologically active protein consisting of a dimer composed of two polypeptides connected by a disulphide bridge, designated as A and B. It is mainly synthesised in the megakaryocytes, and in humans represents the main serum mitogenic agent for cells of mesenchymal origin. It is used to promote healing of wounds/ulcers because it is a mediator of stromal connective tissue formation and, for all these reasons, is currently also used to promote the formation of new bone tissue.

Transforming growth factor-β (TGFβ) is a peptide that performs a crucial role in regulating the immune system, and in tissue regeneration, cell differentiation and embryogenesis. It is mainly used as a wound-healing agent because it increases healing of skin wounds/ulcers and promotes closure of bone fractures; for those reasons it is also used in the treatment of osteoporosis and OA. Finally, experimental data demonstrates that TGFβ also possesses cardioprotective properties after ischaemic damage to the heart.

Epidermal growth factor (EGF) is a growth factor that plays an important part in regulating growth, and in cell proliferation and differentiation. Human EGF is a 6045 Dalton protein, consisting of 53 amino-acid residues and three intramolecular disulphide bridges. It is found in platelets, macrophages, urine, saliva, milk and plasma.

It is a protein used as a gastroprotective agent because it stimulates proliferation of the gastrointestinal mucosa cells; it is used to promote skin tissue regeneration because it stimulates the formation of new granulation tissue in the treatment of skin, venous and other types of wounds/ulcers. Finally, topical applications of EGF have given excellent results in the regeneration of damaged corneal tissue, for example after corneal surgery or in the case of degenerative disorders like keratitis.

Vascular endothelium growth factor (VEGF-B) is a protein growth factor involved in both vasculogenesis (namely ex novo genesis of a circulatory system at embryonal age), neurogenesis and angiogenesis. It is also a neuroprotective agent that protects the neurons against NMDA-mediated ischaemic damage.

Erythropoietin (EPO) is a glycoprotein hormone produced in humans by the kidneys and, to a lesser extent, the liver and brain, whose main function is to regulate erythropoiesis (production of red blood cells by the bone marrow).

EPO has also been produced in the laboratory and used as a medicament to treat anaemia in patients suffering from kidney disease or blood disorders, or to accelerate recovery after the administration of chemotherapy to cancer patients. In recent studies, EPO has been observed to play a neuroprotective role as an anti-inflammatory agent.

Erythropoietin is a glycoprotein molecule weighing about 30000 D. Finally, since 1989, EPO has been made available as a medicament for anaemic patients undergoing dialysis. Subsequently, its use was also extended to patients with chronic kidney failure undergoing conservative treatment, helping to improve their quality of life. The pharmaceutical production of erythropoietin is performed by the recombinant DNA method.

Nerve growth factor (NGF) is a protein secreted in the hypothalamus, by the thyroid and the pituitary gland; it is also produced by the smooth muscle cells and fibroblasts. The active form is NGFβ of 26 KDa, a homodimer with two disulphide bridges that binds two 118-aminoacid protein chains. It is responsible for the differentiation and functionality of the neurons of the peripheral NS and the cholinergic neurons of the CNS. It is therefore used to treat neurodegenerative disorders such as dementia; NGF has also proved useful to treat glaucoma.

Transferrin is the main iron transport protein in the bloodstream. Transferrin, which is synthesised by the liver and the monocyte-macrophage system, binds in a very stable, but reversible way the iron absorbed at intestinal level and that originating from the degradation of the red blood cells, carrying it to the sites of use (in particular the bone marrow) and deposit (in particular the liver).

From the structural standpoint it is a glycoprotein formed by a 679-amino-acid polypeptide chain with a molecular weight of about 80 KD, and possesses two binding sites for ferric ions ($Fe^{3+}$) but no affinity for ferrous ions ($Fe^{2+}$); its half-life is about 8 days.

Transferrin is mainly synthesised by the liver, and its reference values in the blood are 200-360 mg/dL. The transferrin levels increase during the use of the contraceptive pill, during pregnancy, and in the event of iron deficiency. Conversely, they fall in the case of nephrotic syndrome, liver disease, malnutrition, chronic inflammatory disorders, tumours, and treatments with iron or cortisone. A physiological reduction can occur at neonatal age or in old age.

TIMPs are proteins that inhibit metalloproteases, namely enzymes involved in the degradation of cartilage matrix; the TIMP family includes the forms TIMP-2, TIMP-3 and TIMP-4 produced by the chondrocytes, fibroblasts, synoviocytes, osteoblasts, neurons, macrophages, smooth muscle cells, hepatocytes and others.

They consequently play a protective role towards the chondrocytes and the cartilage erosion caused by OA.

DETAILED DESCRIPTION OF THE INVENTION

The invention relates to novel pharmaceutical compositions comprising specific hyaluronic acid amides combined (i.e. not chemically bonded) with proteins of a mainly hydrophobic nature, which are therapeutically and/or biologically active, for the preparation of sustained, slow protein release systems.

The systems according to the invention cause:
  The sustained release of said protein, for a lengthy period of time (compared with the same protein administered "as is"). This continuous release increases the therapeutic window of the medicament, because it is not released in large quantities in the period immediately following its administration (as is generally the case with medicaments administered "as is"). Administration as a release system in combination with specific HA amides modulates the quantity released (in relation to time) and the period of release of the medicament (a gradual increase in the quantity of protein released over time is therefore obtained, leading to a final release period exceeding that which occurs when it is administered "as is"); in conclusion, the kinetic release profile of the protein is significantly modified, as is its therapeutic efficacy profile.
  The novel release system is non-toxic because it is biocompatible and biodegradable, and determines the slow release of the protein/medicament carried, guaranteeing the maintenance of therapeutic activity; the integrity of the three-dimensional structure of the active ingredient, which does not undergo any denaturing, is therefore ensured.
  The release system according to the invention does not cause any chemical modification of the protein carried because it is formed by a combination of particular HA amides and the proteins carried which are combined/mixed with them. No covalent chemical bond is therefore established between the carrier and the medicament, thus guaranteeing the structural integrity of the protein/medicament.
  These novel characteristics considerably increase patient compliance, because the medicament can be administered according to novel pharmacokinetics, and consequently with different doses: longer intervals between administrations and changes to the amount of medicament administered, leading to greater efficacy and fewer side effects.

The pharmacologically and/or biologically active proteins forming the object of the invention must possess mainly hydrophobic characteristics measured according to the GRAVY (Grand Average of Hydropathy) index; the GRAVY value of a peptide or protein is calculated as the sum of the hydropathy values of all the amino acids present in the protein, divided by the number of their residues in the protein sequence. Every amino acid possesses a given hydropathy index, ranging from 4.5 for isoleucine (aa. with residue formed by aromatic hydrocarbon radical which gives the molecule a clear non-polar, and consequently hydrophobic nature) to −4.5 for arginine, an amino acid with a positively-charged residue (Kyte J. et al., J. Mol. Biol., 1982, 157:105-132). This scale indicates that the higher the hydropathy index, the greater the hydrophobicity of the amino acid analysed (FIG. 1). To determine the GRAVY value of the protein analysed easily, the ProtParam (Gasteiger E. et al., *Protein Identification and Analysis Tools on the ExPASy Server*, J M Walker ed., The Proteomics Protocols Handbook, Humana Press, 2005, 571-607) programme is generally used, which provides various physicochemical properties of the proteins studied by analysing their sequence; when the said amino-acid sequence is entered, the programme calculates the GRAVY value of the protein whose degree of hydrophobicity is to be measured.

According to the invention, "proteins with a mainly hydrophobic nature" means those which possess a GRAVY index ranging from not less than −0.5 to positive values: once again, the higher the GRAVY index, the greater the hydrophobicity of the protein analysed.

Some examples of proteins with a mainly hydrophobic nature to which this invention relates are listed below:
Insulin: GRAVY index=0.2
Human growth hormone, hGH: GRAVY index=−0.3
Calcitonin, sCT (salmon CT): GRAVY index=−0.5
IL-1, IL-1Ra receptor antagonist: GRAVY index=−0.4
Granulocyte-colony stimulating factor, G-CSF: GRAVY index=0.2
Platelet-derived growth factor, PDGF: GRAVY index=−0.5, PDGF-BB=−0.1 is preferred
Transforming growth factor TGF-13: GRAVY index=−0.3
Epidermal growth factor, EGF: GRAVY index=−0.5
Vascular endothelial growth factor B, VEGF-B: GRAVY index=−0.2
Erythropoietin (human) or EPO: GRAVY index=−0.03
Nerve growth factor or NGFβ: GRAVY index=−0.3
Transferrin (human): GRAVY index=−0.2
Tissue inhibitor of metalloproteinase-2 (human), TIMP-2: GRAVY index=−0.2
Tissue inhibitor of metalloproteinase-3 (human), TIMP-3: GRAVY index=−0.3
Tissue inhibitor of metalloproteinase-4 (human), TIMP-4: GRAVY index=−0.18.

The Applicant has demonstrated that the hyaluronic acid amides forming the object of the invention, listed below, form a release system that determines the sustained, slow release of proteins with a hydrophobic nature contained in it, while that proteins with a mainly hydrophilic nature, combined with the same amides, do not form release systems suitable for their sustained, slow release over time.

The HA amides suitable to form said release systems forming the object of the invention are:
HA hexadecylamide: HA amide with hexadecylamine, having a molar amidation percentage (determined by 1H-NMR) ranging between 7 and 14%, preferably between 8 and 9%;
HA octylamide: HA amide with octylamine, having a molar amidation percentage (determined by 1H-NMR) ranging between 10 and 15%, preferably between 10 and 11%;
HA dodecylamide: HA amide with dodecylamine, having a molar amidation percentage (determined by 1H-NMR) ranging between 10 and 15%, preferably between 10 and 11%;
HA tert-butylamide: HA amide with tert-butylamine, having a molar amidation percentage (determined by 1H-NMR) ranging between 7 and 12%, preferably between 7 and 8%;
HA benzylamide: HA amide with benzylamine, having a molar amidation percentage (determined by 1H-NMR) ranging between 7 and 15%, preferably between 8 and 9%.

The HA used in the present invention for the preparation of the said amides can derive from any source, such as extraction from cockscombs (EP 138572) or fermentation (for example from *Streptococcus equi* as known to the skilled person), or by a technological process (for example from *Bacillus*, WO 2012/032154), and have a weight-average molecular weight (determined by the limiting viscosity number: Terbojevich et al., Carbohydrate Research, 1986, 149:363-377 method) of between 400 and $3 \times 10^6$ Da, preferably between 50 and 730 KDa, between 750 and 1230 KDa or between 1500 and 2500 KDa, and even more preferably between 150 and 250 KDa and/or between 500 and 730 KDa.

The HA hexadecylamide with a weight-average molecular weight of between 150 and 250 KDa or between 500 and 730 KDa is preferred.

The HA amides listed above, forming the object of the invention, can be prepared as described in EP 1095064, which also describes different uses thereof, including the formation of release systems for pharmacologically active substances, but without making any distinction between the chemical species of the medicaments used and the type of amide selected, and above all, without describing the effect obtained. However, it has now been found that particular HA amides, such as hexadecylamide, octylamide, dodecylamide, tert-butylamide and benzylamide, with particular percentages of amidation and selected MW intervals, combined with proteins having a mainly hydrophobic nature (and therefore a GRAVY index exceeding −0.5), which are therapeutically and/or biologically active, are useful for the preparation of a novel sustained, slow release system for said proteins.

The following proteins are preferred:
Insulin
hGH
sCT
IL-1Ra
G-CSF
PDGF, preferably PDGF-BB
TGF-β
EGF
VEGF-B
EPO NGFβ
Transferrin
TIMP-2, TIMP-3, TIMP-4.

Said proteins can be produced by recombinant DNA techniques or by extraction from tissue.

A further object of the invention is novel release systems comprising:
1. HA hexadecylamide, octylamide, dodecylamide, tert-butylamide or benzylamide, combined with
2. Insulin, hGH, sCT, IL-1Ra, G-CSF, PDGF, preferably PDGF-BB, TGF-β, EGF VEGF-B, EPO, NGFβ, transferrin, TIMP-2, TIMP-3 and TIMP-4, possibly combined with stabilisers (when necessary) and excipients.

In particular, the object of the invention is the system comprising:
1. HA hexadecylamide, preferably HA hexadecylamide with a weight-average molecular weight of between 150 and 250 KDa or between 500 and 730 KDa.
2. hGH or sCT,
3. possibly combined with stabilisers and excipients.

The novel systems are usable in the sustained, slow release of the active agents they contain because they modify the therapeutic window of the protein/medicament combined with them: different dosage regimens are therefore possible, leading to better patient compliance.

The proteins present in the release system will determine the use of the system. For example, the release system comprising HA hexadecylamide with hGH or sCT will preferably be used by intra-articular administration to treat OA, rheumatoid and psoriatic arthritis, and osteoporosis.

The Applicant has demonstrated that this novel release system determines the continuous release of hGH in the synovial fluid of the treated joint, leading to a greater therapeutic effect, but without allowing the active agent to pass into the plasma (thereby reducing its concentration in the joint), thus preventing the systemic side effects of the medicament.

The object of the invention is also the system comprising:
one or more HA amides as previously listed and described, with insulin; this novel system is described by the Applicant as a novel depot in the slow release of insulin for the treatment of diabetic disorders requiring lower administrations of medicament.

The object of the invention is also the system comprising:
one or more HA amides previously listed and described; preferably hexadecylamide, combined with proteins such as PDGF (preferably PDGF-BB), TGF-β, EGF or VEGF-B, for injectable, intra-articular or topical use or for oral administration.

The protein factors described above (PDGF, TGF-β, EGF and VEGF-B) are growth factors whose presence is known, and are particularly concentrated in human platelet-rich plasma (PRP). The novel release system containing them will preferably be usable to treat joint damage caused by OA, in tendinitis, to repair cardiac muscle damage, to repair bone lacerations/fractures/cavities to promote the formation of new bone tissue, and finally, in the healing of skin ulcers/wounds/lacerations to promote the formation of new connective tissue.

Another object of the invention is the system comprising:
one or more HA amides previously listed and described, preferably hexadecylamide, in combination with the metalloprotease inhibitors TIMP-2, TIMP-3 or TIMP-4, for injectable, preferably intra-articular use.

The novel release system will preferably be usable to treat joint cartilage damage caused by OA and repair osteochondral erosions.

The preparation examples of the novel release systems and the experiments conducted by the Applicant to demonstrate the efficacy of said systems according to the invention are described below.

EXAMPLE 1

Synthesis of the Hexadecylamide Derivative of HA with a Weight-Average MW of Between 500 and 730 kDa, Hyadd4, with a Molar Amidation Percentage of Between 8 and 9%

5.00 g of hyaluronic acid sodium salt of fermentative origin with a MW of between 500 and 730 k Da is dissolved in 250 ml of water, and the resulting solution is percolated through a glass column pre-packed with 100 ml of Dowex resin in the form of tetrabutylammonium. The HA solution, in the form of TBA salt, is eluted, collected and freeze-dried.

2 g of the product thus obtained is dissolved in 200 ml of dimethyl sulphoxide (DMSO), and 64 μl of methanesulphonic acid is added; 53 mg of 1,1'-carbonyldiimidazole is added, and the mixture is left under gentle stirring for 1 h at room temperature. 998 mg of hexadecylamine is then added, and the amidation reaction is conducted at 42° C. for 24 hours.

The reaction is stopped by adding 5 ml of a saturated aqueous solution of NaCl, and 30 mins later, 1.5 volumes of absolute ethanol are added to isolate the derivative obtained. The precipitate is washed in ethanol/H2O 80:20 and finally in absolute ethanol, then dried under high vacuum at 40° C.

1.3 g of derivative is obtained, and its degree of amidation is determined by 1H-NMR.

EXAMPLE 2

Synthesis of the Octylamide Derivative of HA with a Weight-Average MW of Between 500 and 730 kDa, Hyadd2, with a Molar Amidation Percentage of Between 10 and 11%

5.00 g of hyaluronic acid sodium salt of fermentative origin with a MW of between 500 and 730 k Da is dissolved in 250 ml of water, and the resulting solution is percolated through a glass column pre-packed with 100 ml of Dowex resin in the form of tetrabutylammonium. The HA solution, in the form of TBA salt, is eluted, collected and freeze-dried.

2 g of the product thus obtained is dissolved in 200 ml of dimethyl sulphoxide (DMSO), and 64 μl of methanesulphonic acid is added; 61.4 mg of 1,1'-carbonyldiimidazole is added, and the mixture is left under gentle stirring for 1 h at room temperature. 330 mg of octylamine is then added, and the amidation reaction is conducted at 42° C. for 24 hours.

The reaction is stopped by adding 5 ml of a saturated aqueous solution of NaCl, and 30 mins later, 1.5 volumes of absolute ethanol are added to isolate the derivative obtained. The precipitate is washed in ethanol/H2O 80:20 and finally in absolute ethanol, then dried under high vacuum at 40° C.

1.2 g of derivative is obtained, and its degree of amidation is determined by 1H-NMR.

EXAMPLE 3

Synthesis of the Dodecylamide Derivative of HA with a Weight-Average MW of Between 500 and 730 kDa, Hyadd3, with a Molar Amidation Percentage of Between 10 and 11%

5.00 g of hyaluronic acid sodium salt of fermentative origin with a MW of between 500 and 730 k Da is dissolved in 250 ml of water, and the resulting solution is percolated through a glass column pre-packed with 100 ml of Dowex resin in the form of tetrabutylammonium. The HA solution, in the form of TBA salt, is eluted, collected and freeze-dried.

2 g of the product thus obtained is dissolved in 200 ml of dimethyl sulphoxide (DMSO), and 64 μl of methanesulphonic acid is added; 54.2 mg of 1,1'-carbonyldiimidazole is added, and the mixture is left under gentle stirring for 1 h at room temperature. 448 mg of dodecylamine is then added, and the amidation reaction is conducted at 42° C. for 24 hours.

The reaction is stopped by adding 5 ml of a saturated aqueous solution of NaCl, and 30 mins later, 1.5 volumes of absolute ethanol is added to isolate the derivative obtained. The precipitate is washed in ethanol/H2O 80:20 and finally in absolute ethanol, then dried under high vacuum at 40° C.

1.25 g of derivative is obtained, and its degree of amidation is determined by 1H-NMR.

EXAMPLE 4

Synthesis of the Tert-Butylamide Derivative of HA with a Weight-Average MW of Between 500 and 730 kDa, Hyadd6, with a Molar Amidation Percentage of Between 7 and 8%

5.00 g of hyaluronic acid sodium salt of fermentative origin with MW between 500 and 730 k Da is dissolved in 250 ml of water, and the resulting solution is percolated through a glass column pre-packed with 100 ml of Dowex resin in the form of tetrabutylammonium. The HA solution, in the form of TBA salt, is eluted, collected and freeze-dried.

2 g of the product thus obtained is dissolved in 200 ml of dimethyl sulphoxide (DMSO), and 64 μl of methanesulphonic acid is added; 53 mg of 1,1'-carbonyldiimidazole is added, and the mixture is left under gentle stirring for 1 h at room temperature. 178 mg of tert-butylamine is then added, and the amidation reaction is conducted at 42° C. for 24 hours.

The reaction is stopped by adding 5 ml of a saturated aqueous solution of NaCl, and 30 mins later, 1.5 volumes of absolute ethanol are added to isolate the derivative obtained. The precipitate is washed in ethanol/H2O 80:20 and finally in absolute ethanol, then dried under high vacuum at 40° C.

1.25 g of derivative is obtained, and its degree of amidation is determined by 1H-NMR.

EXAMPLE 5

Synthesis of the Benzylamide Derivative of HA with a Weight-Average MW of Between 500 and 730 kDa, Hyadd1, with a molar amidation percentage of between 8 and 9%

5.00 g of hyaluronic acid sodium salt of fermentative origin with MW between 500 and 730 k Da is dissolved in 250 ml of water, and the resulting solution is percolated through a glass column pre-packed with 100 ml of Dowex resin in the form of tetrabutylammonium. The HA solution, in the form of TBA salt, is eluted, collected and freeze-dried.

2 g of the product thus obtained is dissolved in 200 ml of dimethyl sulphoxide (DMSO), and 64 μl of methanesulphonic acid is added; 54.0 mg of 1,1'-carbonyldiimidazole is added, and the mixture is left under gentle stirring for 1 h at room temperature. 260 mg of benzylamine is then added, and the amidation reaction is conducted at 42° C. for 24 hours.

The reaction is stopped by adding 5 ml of a saturated aqueous solution of NaCl, and 30 mins later, 1.5 volumes of absolute ethanol are added to isolate the derivative obtained. The precipitate is washed in ethanol/H2O 80:20 and finally in absolute ethanol, then dried under high vacuum at 40° C.

1.25 g of derivative is obtained, and its degree of amidation is, determined by 1H-NMR.

EXAMPLE 6

Preparation of Formulations Containing HA and hGH in the Ratios of 10:1 and 20:1 w/w 8 mg of hyaluronic acid sodium salt of fermentative origin with a MW of between 150 and 250 KDa (LMW) and between 500 and 730 kDa (MMW) is dissolved in 1 ml of phosphate buffer at pH=7.4. When dissolution is complete, 0.8 mg of hGH is added to obtain a polysaccharide/protein weight ratio of 10:1, and 0.4 mg of hGH to obtain a polysaccharide/protein weight ratio of 20:1. The two ingredients are suitably mixed so that the composition is uniform. The loading is calculated by diluting the mixture 1:10 in buffer and measuring the UV absorbance at 280 nm which, with the use of a calibration curve, provides the GH concentration value.

EXAMPLE 7

Preparation of the Formulation Containing the Release System Formed by Hexadecylamide of HA and hGH in the Ratio of 10:1 w/w 8 mg of a hexadecylamide derivative of HA, Hyadd4, prepared as described in Example 1, is dissolved in 1 ml of phosphate buffer at pH=6.9. When dissolution is complete, 0.8 mg of hGH, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the GH concentration value.

EXAMPLE 8

Preparation of the Formulation Containing the Release System Formed by Tert-Butylamide of HA and hGH , 10:1 w/w 8 mg of Hyadd6, prepared as described in Example 4, is dissolved in 1 ml of phosphate buffer at pH=6.9 (8 mg/ml). When dissolution is complete, 0.8 mg of hGH, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the GH concentration value.

EXAMPLE 9

Preparation of the Formulation Containing the Release System Formed by Octylamide of HA and hGH , 10:1 w/w 8 mg of Hyadd2, prepared as described in example 2, is dissolved in 1 ml of phosphate buffer at pH=6.9 (8 mg/ml). When dissolution is complete, 0.8 mg of hGH, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the GH concentration value.

EXAMPLE 10

Preparation of the Formulation Containing the Release System Formed by Dodecylamide of HA and hGH, 10:1 w/w 8 mg of Hyadd3, prepared as described in Example 3, is dissolved in 1 ml of phosphate buffer at pH=6.9 (8 mg/ml). When dissolution is complete, 0.8 mg of hGH, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the GH concentration value.

EXAMPLE 11

Preparation of the Formulation Containing the Release System Formed by Benzylamide of HA and hGH, 10:1 w/w 8 mg of Hyadd1, prepared as described in Example 5, is dissolved in 1 ml of phosphate buffer at pH=6.9 (8 mg/ml). When dissolution is complete, 0.8 mg of hGH, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the GH concentration value.

EXAMPLE 12

Preparation of the Formulation Containing the Release System Formed by Hexadecylamide of HA and sCT in the Ratio of 10:1 w/w 8 mg of Hyadd4, prepared as described in Example 1, is dissolved in 1 ml of phosphate buffer at pH=6.9. When dissolution is complete, 0.8 mg of salmon calcitonin (sCT), pre-dissolved in phosphate buffer, is added to obtain a w/w ratio of 10:1, and suitably mixed so that the composition is uniform and the protein is trapped in the gel. The loading of the gel is calculated by diluting it 1:10 in buffer and measuring the UV absorbance at 280 nm which, with the use of a calibration curve, provides the calcitonin concentration value.

EXAMPLE 13:

Preparation of the Formulation Containing the Release System Formed by Hexadecylamide of HA and IL-1Ra, 10:1 w/w 8 mg of Hyadd4, prepared as described in Example 1, is dissolved in 1 ml of phosphate buffer at pH=6.9. When dissolution is complete, 0.8 mg of IL-1Ra, pre-dissolved in an aqueous solution, is added, and suitably mixed so that the composition is uniform and the protein is trapped in the gel. The loading of the gel is calculated by diluting it 1:10 in buffer and measuring the UV absorbance at 280 nm which, with the use of a calibration curve, provides the IL-1Ra concentration value.

EXAMPLE 14

Preparation of a Formulation Based on Hexadecylamide of HA and RNase, 10/1 w/w 8 mg of Hyadd4, prepared as described in Example 1, is dissolved in 1 ml of phosphate buffer at pH=6.9. When dissolution is complete, 0.8 mg of RNase, pre-dissolved in phosphate buffer, is added, and suitably mixed so that the protein is trapped in the gel. The loading of the gel is calculated by diluting it 1:10 in buffer and measuring the UV absorbance at 280 nm which, with the use of a calibration curve, provides the RNAse concentration value.

EXAMPLE 15

Preparation of the Formulation Containing the Release System Formed by Hexadecylamide of HA and Insulin, 10:1 w/w 8 mg of Hyadd1, prepared as described in Example 1, is dissolved in 1 ml of phosphate buffer at pH=6.9. When dissolution is complete, 0.8 mg of insulin, pre-dissolved in phosphate buffer, is added, and suitably mixed so that the protein is trapped in the gel. The loading of the gel is calculated by diluting it 1:10 in buffer and measuring the UV absorbance at 280 nm which, with the use of a calibration curve, provides the insulin concentration value.

EXAMPLE 16

Study of the Release of hGH Formulated with HA or HA Amides

The formulations, prepared as described in Examples 6-11, are introduced into dialysis tubes with a cut-off of 100 kDa and immersed in phosphate buffer at pH 7 under gentle stirring to monitor their release from the donor compartment. For comparison purposes, 0.8 mg of hGH is mixed with 1 ml of phosphate buffer (PBS), and the formulation is introduced into a dialysis tube.

Sink conditions are maintained throughout all the experiments. At pre-set times, 50 µl aliquots are taken from the donor compartment and diluted 1:10 to determine the protein content over time. The analysis is conducted in parallel by UV reading at 280 nm and RP-HPLC at 220 nm to determine the quantity of protein remaining and its degradation, if any. Scattering measurements are also taken to study the aggregation of the protein formulated. Finally, samples are taken from the receptor compartment to check that the quantity of protein released corresponds to the quantity that disappears from the donor compartment, and mass spectrometry measurements (Esi-Tof) are taken to confirm that the GH released has not undergone any structural degradation. The release curves are constructed by showing the percentage of protein released over time. FIGS. 2, 3, 4 and 5.

Results

FIG. 2 shows the release profile of hGH determined by the system formed by Hyadd4 and hGH vs the control represented by the same protein prepared in PBS.

Figure 3:
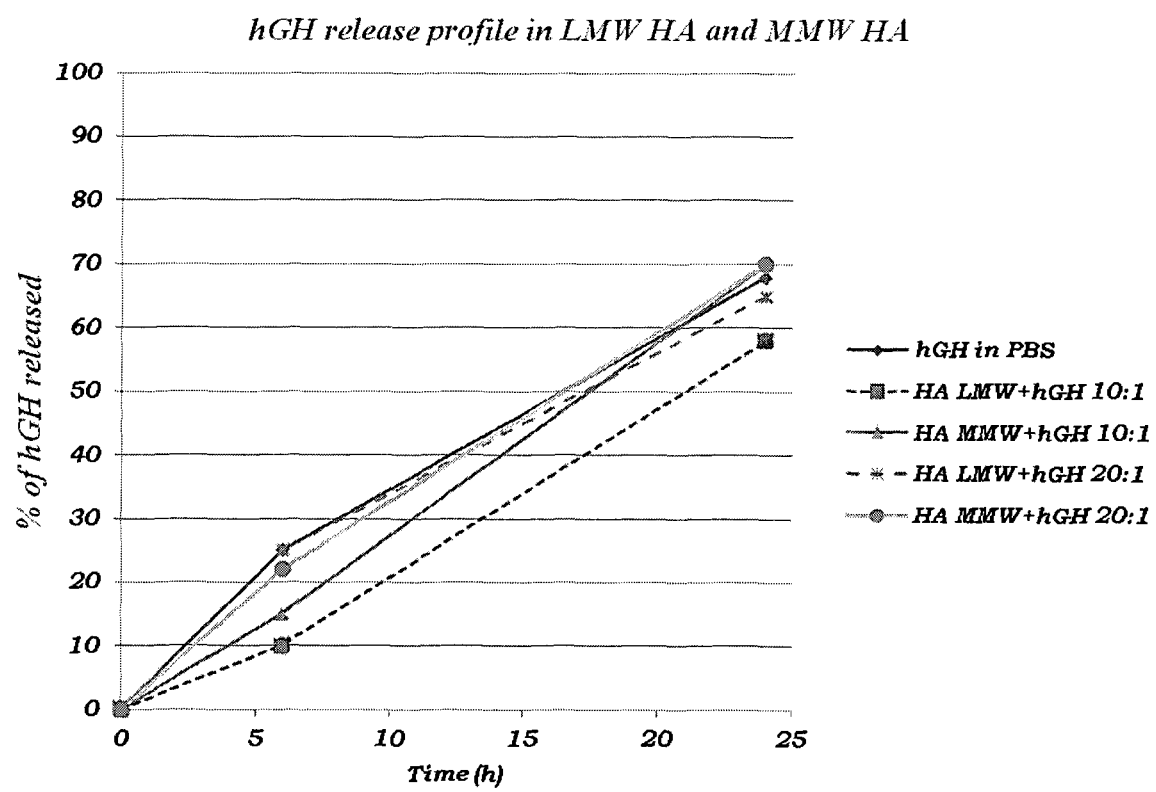
FIG. 3: Release profiles of hGH protein formulated in combination with LMW-HA and MMW-HA: in both cases two different weight ratios of HA with hGH (10:1 and 20:1) were tested because, with this experiment, the Applicant intends to demonstrate that the combination of proteins with a hydrophobic nature, even with large amounts of HA having different MWs, does not elicit any change in the release profile of the protein vs the profile obtained by preparing it in PBS, namely in aqueous solvent.

FIG. 3 shows the release profiles of hGH protein formulated in combination with LMW-HA and MMW-HA: in both cases two different weight ratios of HA with hGH (10:1 and 20:1) were tested because, with this experiment, the Applicant intends to demonstrate that the combination of proteins with a hydrophobic nature, even with large amounts of HA having different MWs, does not elicit any change in the release profile of the protein vs the profile obtained by preparing it in PBS, namely in aqueous solvent.

Figure 4:
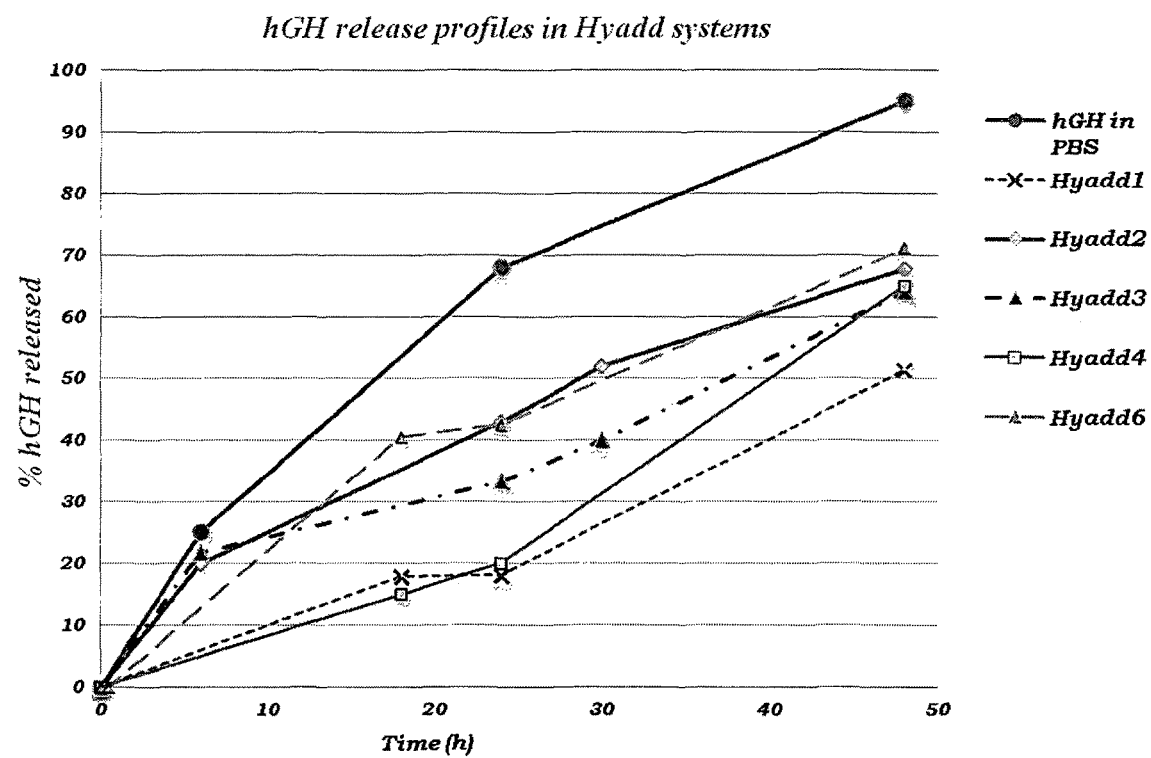
FIG. 4: Release profiles of hGH from release systems formed by the amides according to the present invention and hGH with the control represented by hGH in PBS.

FIG. 4 compares the release profiles of hGH from release systems formed by the amides according to the present invention and hGH with the control represented by hGH in PBS.

Figure 5:
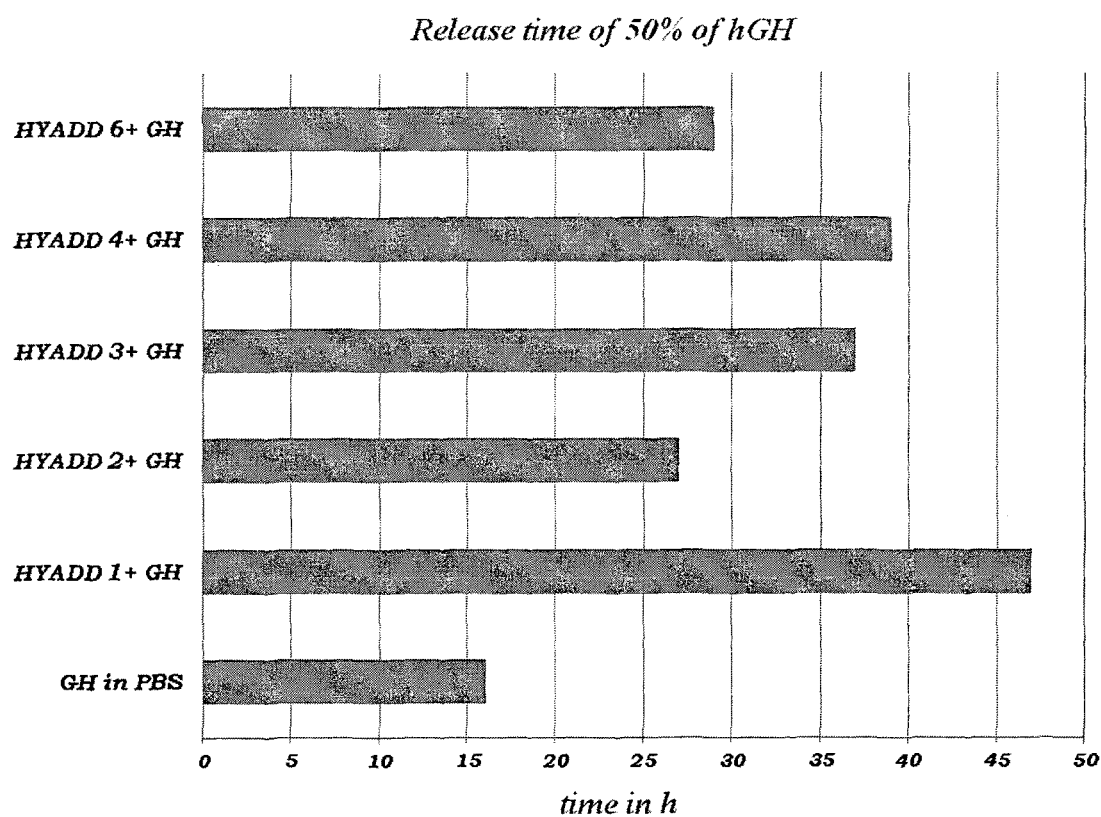
FIG. 5: Release time of 50% of hGH from release systems formed by the amides according to the present invention, again vs the control as stated above.

FIG. 5 shows the release time of 50% of hGH from release systems formed by the amides according to the present invention, again vs the control as stated above.

If FIG. 3 is compared with FIGS. 2 and 4, it will be seen that the release systems formed by HA amides (described and claimed above) with proteins having a mainly hydrophobic nature (in this case hGH), cause the sustained, slow release over time of the protein in a clearly significant way, vs the control represented by proteins analysed in PBS, and vs the protein formulated in HA with a different MW and a different weight ratio. It is therefore not the concentration and/or the MW of the polysaccharide that determines a modification in the release profile of the hydrophobic protein studied, but the chemical nature of the polymer. All this is even more evident in FIG. 5, which compares the release times of 50% of hGH: the figure shows that the novel release systems to which the present invention relates increase the release times up to three-fold vs the control (hGH in PBS).

EXAMPLE 17

Study of Release of sCT, IL1-Ra and Insulin vs the Release Profile of Hydrophilic A Each of the formulations prepared as described in Examples 12-15 is introduced into a dialysis tube with a cut-off of 100 kDa and immersed in phosphate buffer at pH 7 under gentle stirring. By way of comparison, 0.8 mg of calcitonin, IL-1Ra, insulin or RNase is mixed with 1 ml of phosphate buffer and the formulations are introduced into a dialysis tube to monitor its release from the donor compartment over time.

Sink conditions are maintained throughout all the experiments. At pre-set times, 10 µl aliquots are taken from the donor compartment and diluted 1:10 to determine the protein content over time. The analysis is conducted in parallel by UV reading at 280 nm to determine the quantity of protein remaining. Scattering measurements are also taken to study the aggregation of the protein formulated. Finally, samples are taken from the receptor compartment to check that the quantity of protein released corresponds to the quantity that disappears from the donor compartment. The release curves are constructed, showing the percentage of protein released over time vs its control.

The protein RNase A possesses a GRAVY index=−0.67 and consequently cannot be classified as a mainly hydrophobic protein, but as a hydrophilic protein. It is described below in order to compare its release profile with that resulting from the Hyadd release system combined with proteins having a mainly hydrophobic nature, so as to demonstrate the differences.

Results

Figure 6:
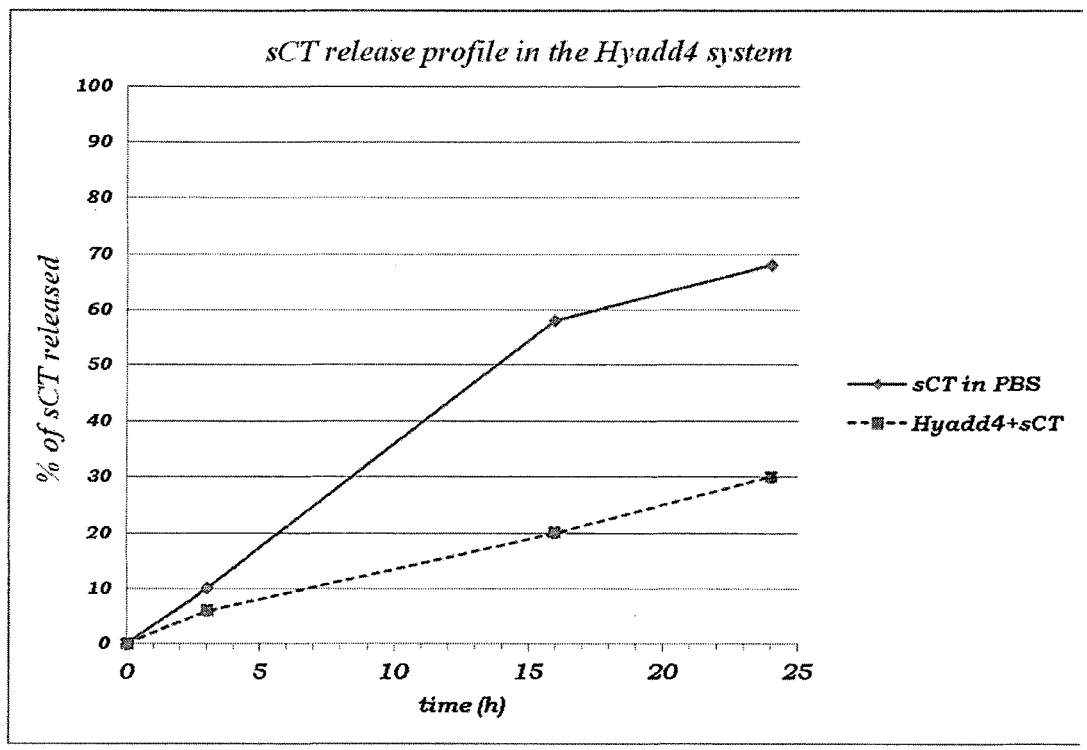
FIG. 6: Release profile of sCT in the HYADD system.
Figure 7:
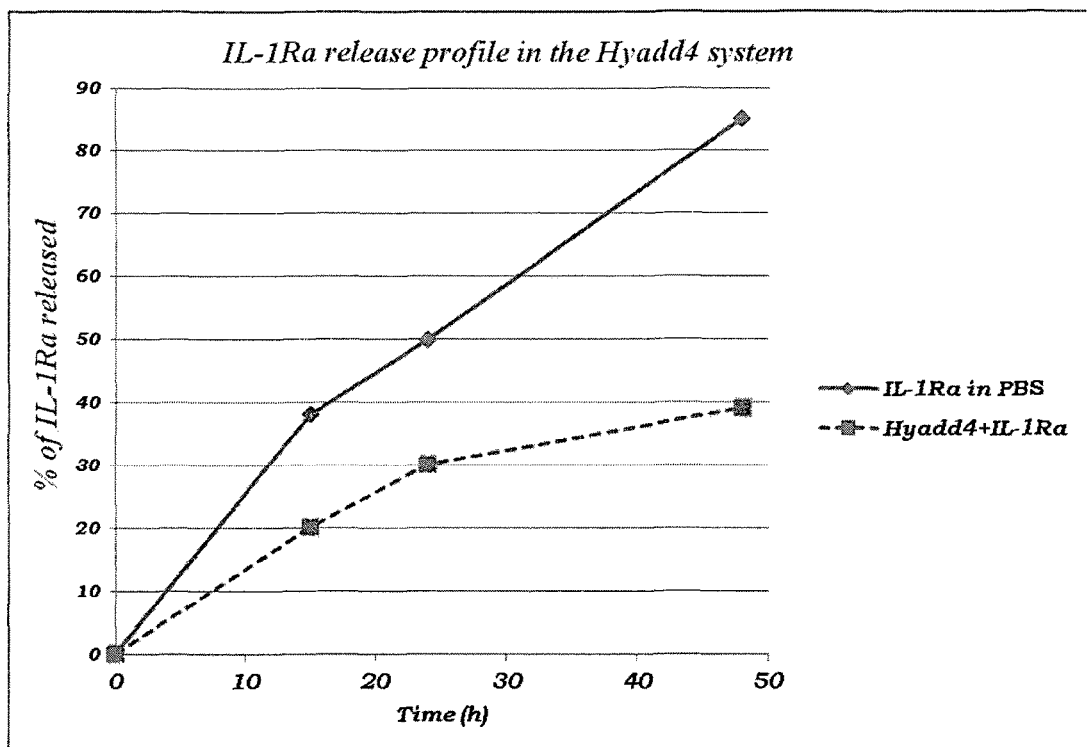
FIG. 7: Release profile of IL-1Ra in the HYADD system.
Figure 8:
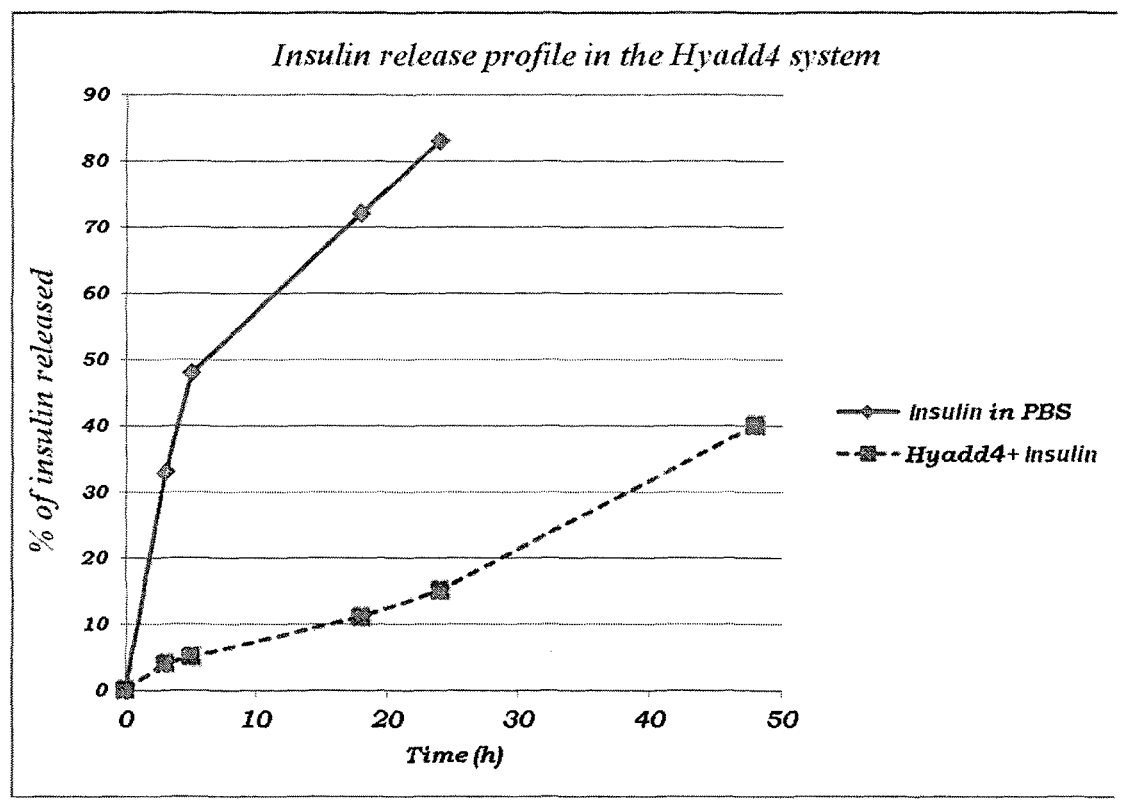
FIG. 8: Release profile of Insulin in the HYADD system.

FIGS. 6-8 show the release profiles of the 3 proteins of a mainly hydrophobic nature analysed: in all three cases the system formed by HA hexadecylamide, combined with said proteins, determines its sustained, slow release for much longer times than the control.

Figure 9:
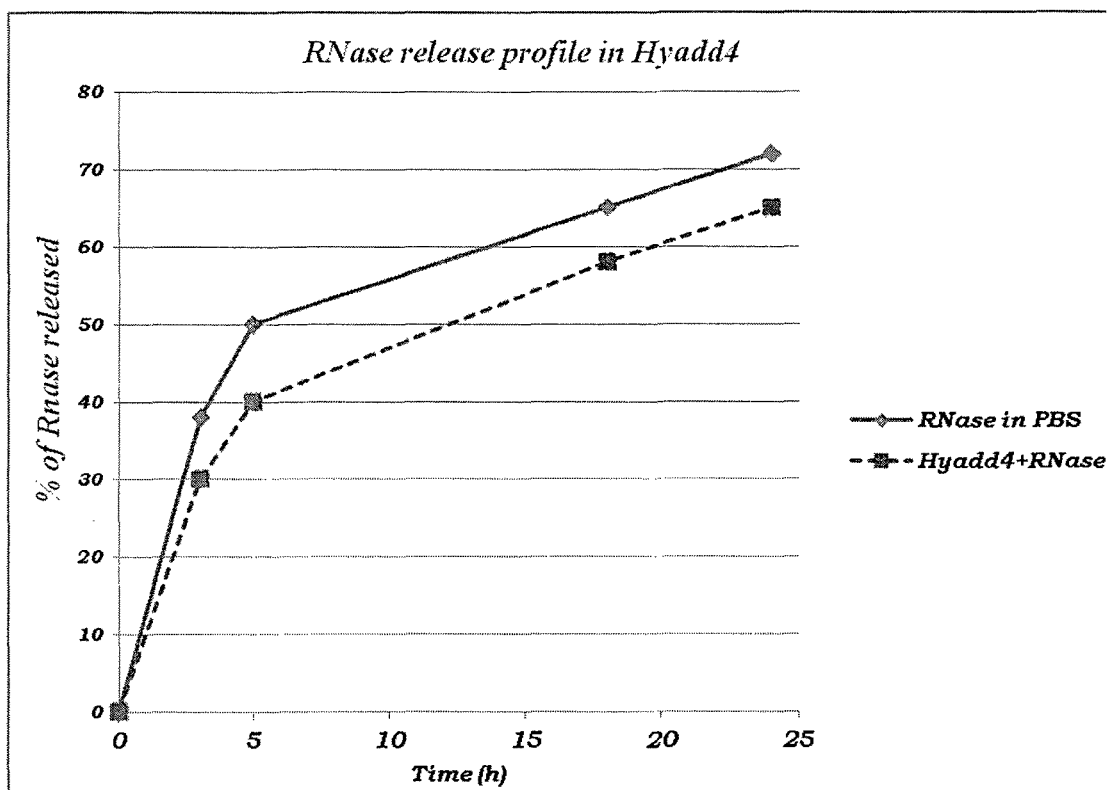
FIG. 9: Release profile of RNase in the HYADD system.

Conversely, FIG. 9 demonstrates that the combination of the same hexadecylamide in an identical weight ratio (10:1 w/w) with the protein RNase, which has a mainly hydrophilic nature and a GRAVY index=−0.67, determines a release profile identical to that produced by the same protein when formulated in PBS.

EXAMPLE 18

Study of Release of hGH Into Human Synovial Fluid (LS) Originating from Patients with Osteoarthritis The hormone hGH is first covalently bonded to a fluorescent probe (Cy5.5) so that it can be unequivocally recognised in the presence of other synovial proteins. For this purpose 1.5 mg of hGH is dissolved in 2 ml of borate buffer at pH 8, to which 2 mg of Cy5.5 pre-dissolved in 60 µl of DMSO is added. The labelling reaction is conducted shaded from the light, under gentle stirring, for 18 h. Purification is then conducted by dialysis against phosphate buffer for 4 days and against MilliQ water for 1 day. The labelled protein is then analysed by gel filtration to verify its purity.

A formulation based on Hyadd4 and hGH-Cy5.5 is prepared as described in example 7 with a weight ratio of 10:1. The two ingredients are suitably mixed so that the composition is uniform and the protein is trapped in the gel. The gel thus obtained is introduced into a dialysis tube with a cut-off of 100 kDa, immersed in a medium consisting of PBS and synovial fluid originating from patients with osteoarthritis (v/v 1:1), and maintained under gentle stirring.

The amount of protein released over time into the receptor compartment is determined at pre-set times. The analyses are conducted by RP-HPLC with fluorescence detector, not only to determine the hGH content but also to check that the protein has not undergone degradation. The release curve is constructed, showing the percentage of protein released over time up to 48 h.

Results

Figure 10:
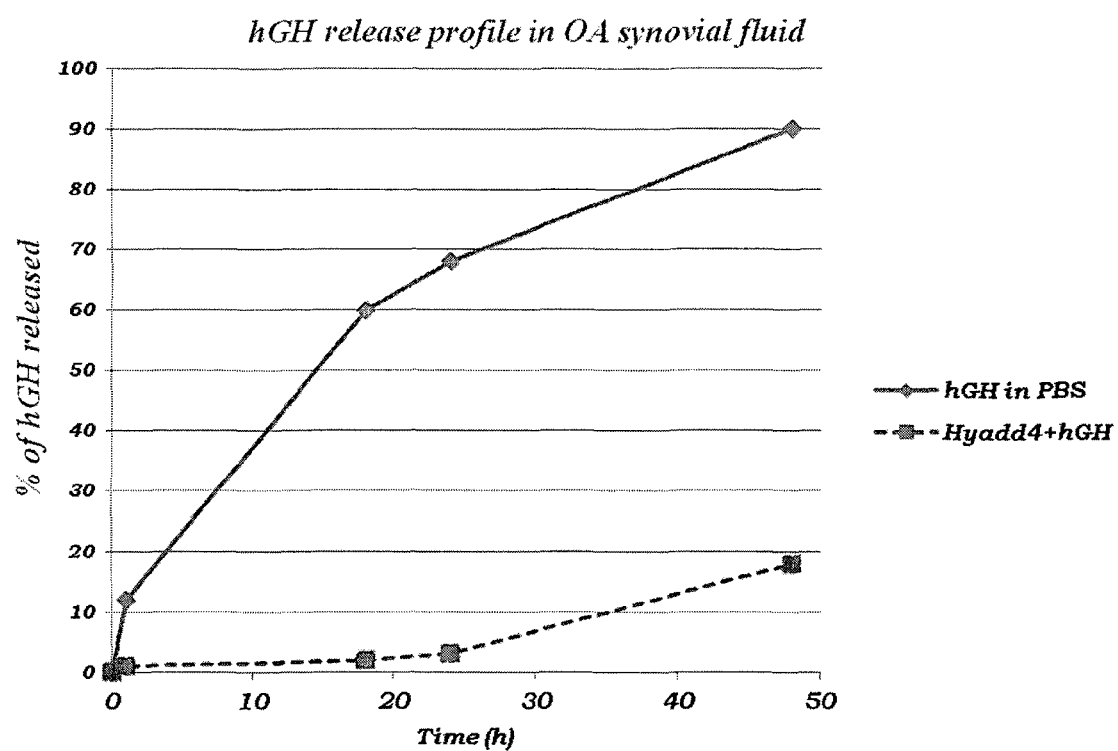
FIG. 10: Release profile of hGH in the HYADD system.

FIG. 10 shows the result obtained: the release in LS of hGH from the system formed by Hyadd4 in combination with the protein studied demonstrates that the sustained, slow release profile previously demonstrated in FIG. 2 is maintained unchanged. It can therefore be stated that the protein/medicament included in the Hyadd system is protected and not subject to degradation in a release medium enriched with enzymes, proteins, some of an unknown nature, and pro-inflammatory molecules, such as the synovial fluid of OA patients.

EXAMPLE 19

Study of the Pharmacokinetics of the System Formed by Hyadd4 and hGH, After Intra-Articular Administration to the Rat 8 mg of Hyadd4, prepared as described in example 1, is dissolved in 1 ml of phosphate buffer at pH=6.9 and sterilised with damp heat at 121° C. Subsequently, 0.8 mg of hGH, pre-dissolved in an aqueous solution and sterilised by filtration through 0.2 micron regenerated cellulose filters, is added in an aseptic environment and suitably mixed so that the composition is uniform and the protein is trapped in the gel.

For the in vivo study, an amount of formulation equivalent to 100 μg of protein/animal is injected into the knee of the rat. At pre-set times (0.15, 1, 2, 3, 4, 5, 6, 7, 8, 24 and 48 h), plasma samples are taken and subjected to the ELISA test to evaluate the concentration of hGH that passed into the plasma after i.a. administration. The experiment is performed in triplicate.

For comparison purposes, one group of animals is treated with an equivalent quantity of free hGH (100 μg), again by intra-articular administration. The pharmacokinetics curves were obtained by plotting the concentration of hGH in ng/ml found in the plasma as a function of time, up to 48 h.

Results

Figure 11:
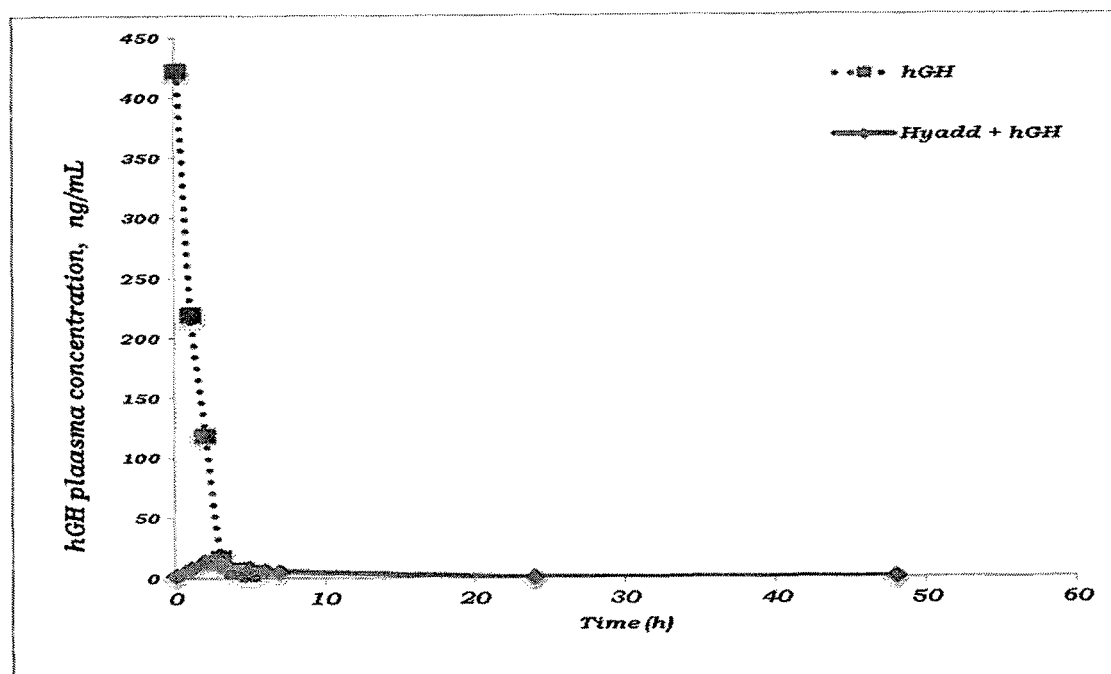
FIG. 11: hGH plasma concentration over time after intra-articular injection.

As shown in FIG. 11, the protein injected can be found in the plasma immediately after the intra-articular injection.

However, due to the sustained release of the protein induced by the Hyadd system, it remains in situ, namely in the joint cavity, and does not pass into the bloodstream, so that the whole of its effect takes place at the injection site.

The invention claimed is:

1. System for sustained release of therapeutically and/or biologically active proteins comprising
    a) a protein with a mainly hydrophobic nature and
    b) a hyaluronic acid (HA) amide
    wherein the protein with a mainly hydrophobic nature has a GRAVY index exceeding -0.5 and the HA amide is selected from
        HA hexadecylamide: HA amide with hexadecylamine having a molar amidation percentage ranging between 7 and 14%, preferably between 8 and 9%;
        HA octylamide: HA amide with octylamine, having a molar amidation percentage ranging between 10 and 15%, preferably between 10 and 11%;
        HA dodecylamide: HA amide with dodecylamine, having a molar amidation percentage ranging between 10 and 15%, preferably between 10 and 11%;
        HA tert-butylamide: HA amide with tert-butylamine, having a molar amidation percentage ranging between 7 and 12%, preferably between 7 and 8%;
        HA benzylamide: HA amide with benzylamine, having a molar amidation content of 7 to 15%, preferably 8 to 9%.

2. System for sustained release of proteins as claimed in claim 1, wherein the HA used for the preparation of the amides has a weight-average molecular weight ranging between 400 and 3-10$^6$ Da, in particular between 50 and 730 KDa, between 750 and 1230 KDa or between 1500 and 2500 KDa, and even more particularly between 150 and 250 KDa or between 500 and 730 KDa.

3. System for sustained release of proteins as claimed in claim 1, wherein the therapeutically and/or biologically active proteins with a mainly hydrophobic nature are insulin, hGH, sCT, IL-1Ra, G-CSF, PDGF, preferably PDGF-BB, TGF-β, EGF, VEGF-B, EPO, NGFβ, transferrin, TIMP-2, TIMP-3 and TIMP-4.

4. System for sustained release of proteins as claimed in claim 1, wherein the HA amide is hexadecylamide and the HA used for the preparation of the amides has a weight-average molecular weight ranging between 150 and 250 KDa or between 500 and 730 KDa.

5. System for sustained release of proteins as claimed in claim 4, wherein the therapeutically and/or biologically active protein is hGH or sCT, optionally combined with stabilisers and excipients.

6. System for sustained release of proteins as claimed in claim 3, wherein the therapeutically and/or biologically active protein is insulin, optionally combined with stabilisers and excipients.

7. System for sustained release of proteins as claimed in claim 4, wherein the therapeutically and/or biologically active protein is PDGF, preferably PDGF-BB, TGF-β, EGF or VEGF-B, optionally combined with stabilisers and excipients.

8. System for sustained release of proteins as claimed in claim 4, wherein the therapeutically and/or biologically active protein is the metalloprotease inhibitor TIMP-2, TIMP-3 or TIMP-4, optionally combined with stabilisers and excipients.

9. A method for sustained release of therapeutically and/or biologically active proteins comprising, administering to a patient in need thereof a system comprising a protein with a mainly hydrophobic nature and a hyaluronic acid (HA) amide, wherein the protein with a mainly hydrophobic nature has a GRAVY index exceeding −0.5, and wherein the HA amide is selected from
    a) HA hexadecylamide: HA amide with hexadecylamine, having a molar amidation percentage ranging between 7 and 14%, preferably between 8 and 9%;
    b) HA octylamide: HA amide with octylamine, having a molar amidation percentage ranging between 10 and 15%, preferably between 10 and 11%;
    c) HA dodecylamide: HA amide with dodecylamine, having a molar amidation percentage ranging between 10 and 15%, preferably between 10 and 11%;
    d) HA tert-butylamide: HA amide with tert-butylamine, having a molar amidation percentage ranging between 7 and 12%, preferably between 7 and 8%;
    e) HA benzylamide: HA amide with benzylamine, having a molar amidation percentage ranging between 7 and 15%, preferably between 8 and 9%;
wherein the HA used for the preparation of the amides has a weight-average molecular weight of between 400 and 3×10$^6$ Da, in particular between 50 and 730 KDa, between 750 and 1230 KDa or between 1500 and 2500 KDa, and even more particularly between 150 and 250 KDa or between 500 and 730 KDa.

10. The method as claimed in claim 9, wherein the therapeutically and/or biologically active proteins with a mainly hydrophobic nature are selected from insulin, hGH, sCT, IL-1Ra, G-CSF, PDGF, PDGF-BB, TGFβ, EGF, VEGF-B, EPO, NGFβ, transferrin, TIMP-2, TIMP-3 and TIMP-4.

11. The method as claimed in claim 10, wherein the HA amide is hexadecylamide.

12. The method as claimed in claim 11, wherein the therapeutically and/or biologically active protein with a mainly hydrophobic nature is hGH or sCT, optionally combined with stabilisers and excipients.

13. The method as claimed in claim 9 which comprises the intra-articular treatment of osteoarthritis, rheumatoid or psoriatic arthritis and/or osteoporosis.

14. The method as claimed in claim 10, wherein the administration is injection, intra-articular, topical, or oral.

15. The method as claimed in claim 11, which comprises treating joint cartilage damage caused by osteoarthritis and/or which comprises the repair of osteochondral erosions by injecting or intra-articularly administering the hyaluronic acid (HA) amide and protein with a mainly hydrophobic nature wherein the therapeutically and/or biologically active protein is metalloprotease inhibitor TIMP-2, TIMP-3 or TIMP-4, optionally combined with stabilisers and excipients for injection or intra-articular administration.

16. The method as claimed in claim 9, which comprises the treatment of joint damage, which is caused by osteoarthritis; tendinitis; cardiac muscle damage; bone fractures/cavities; or skin ulcers, wounds or lacerations.

* * * * *